US 6,626,927 B1

(12) United States Patent  
Koplen (10) Patent No.: US 6,626,927 B1
(45) Date of Patent: Sep. 30, 2003

(54) TATTOO SYSTEM

(76) Inventor: Michael L. Koplen, 1405 9th Ave. SW., Aberdeen, SD (US) 57401

( * ) Notice: Subject to any disclaimer, the term of this patent is extended or adjusted under 35 U.S.C. 154(b) by 37 days.

(21) Appl. No.: 10/096,470

(22) Filed: Mar. 11, 2002

(51) Int. Cl.[7] .............................................. A61B 17/34
(52) U.S. Cl. ...................................................... 606/185
(58) Field of Search ................................. 606/185, 181, 606/184, 187, 188, 189, 186; 81/9.22, 438; 30/362

(56) References Cited

U.S. PATENT DOCUMENTS

| | | | |
|---|---|---|---|
| 5,279,552 A | 1/1994 | Magnet ........................ 604/47 |
| 5,471,102 A | 11/1995 | Becker ........................ 310/50 |
| 5,575,794 A | 11/1996 | Walus et al. ................. 606/116 |
| D380,046 S * | 6/1997 | Domanowski ............. D24/144 |
| 5,741,290 A * | 4/1998 | Hsieh ........................ 606/186 |
| 5,776,158 A | 7/1998 | Chou ......................... 606/186 |
| 5,810,862 A * | 9/1998 | Pilmanis ..................... 606/186 |
| 6,033,421 A | 3/2000 | Theiss et al. ................. 606/186 |
| 6,099,544 A | 8/2000 | Wolf et al. ................... 606/185 |
| 6,197,034 B1 | 3/2001 | Gvozdie et al. ............. 606/116 |
| 6,436,105 B1 * | 8/2002 | Passmore ..................... 606/116 |

* cited by examiner

Primary Examiner—Michael J. Milano
Assistant Examiner—D. Jacob Davis (57) ABSTRACT

A tattoo system for providing a disposable tip that allows for efficient cleaning and tattooing. The tattoo system includes a tube member having a tapered neck with exterior threading at a distal end thereof, and a tip member threadably attached to the tube member. The tip member is comprised of a center body, a rear portion having a tapering rear lip and a rear opening, a front portion with a front opening, a reservoir connected between the front opening and the rear opening, and interior threading within a central portion of said reservoir for threadably engaging the exterior threading. The tip member is preferably comprised of a plastic to sealably engage the tube member. The front portion of the tip member is preferably tapered with the front opening slightly larger than the needle reciprocating through thereof.

16 Claims, 8 Drawing Sheets

TATTOO SYSTEM

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to tattoo machines and more specifically it relates to a tattoo system for providing a disposable tip that allows for efficient cleaning and tattooing.

2. Description of the Prior Art

Tattoo machines have been in use for years. A tattoo machine has a reciprocating needle moves up and down within a tubular structure, carrying ink into the skin of an individual in the process. The tattoo machine has attached within solid needles that puncture the skin at the rate of 50 to 3,000 times a minute. The sterilized needles are installed in the machine and dipped in ink, which is sucked up through the machine's tube system. Then, the tattoo machine uses an up-and-down motion to puncture the top layer of the skin and drive insoluble, micrometer-sized particles of ink into the dermal layer of skin, about one-eighth inch deep.

The main problem with conventional tattoo machines is that they are difficult to clean after using thereby creating a risk of blood contamination within the tube system. Another problem with conventional tattoo machines is that they are difficult to change the color during usage. Another problem with conventional tattoo machines is that during the application of ink to the dermal layer of the skin it is difficult to view a pattern upon the skin because of the excess ink on the upper surface of the skin.

Examples of patented devices which are related to the present invention include U.S. Pat. No. 5,776,158 to Chou; U.S. Pat. No. 5,279,552 to Magnet; U.S. No. Pat. 5,471,102 to Becker; U.S. Pat. No. 5,575,794 to Walus; U.S. Pat. No. 6,033,421 to Theiss; U.S. Pat. No. 6,197,034 to Gvozdie; and U.S. Pat. No. 6,099,544 to Wolf.

While these devices may be suitable for the particular purpose to which they address, they are not as suitable for providing a disposable tip that allows for efficient cleaning and tattooing. Conventional tattoo machines are difficult to clean and are not efficient for applying a tattoo.

In these respects, the tattoo system according to the present invention substantially departs from the conventional concepts and designs of the prior art, and in so doing provides an apparatus primarily developed for the purpose of providing a disposable tip that allows for efficient cleaning and tattooing.

SUMMARY OF THE INVENTION

In view of the foregoing disadvantages inherent in the known types of tattoo machines now present in the prior art, the present invention provides a new tattoo system construction wherein the same can be utilized for providing a disposable tip that allows for efficient cleaning and tattooing.

The general purpose of the present invention, which will be described subsequently in greater detail, is to provide a new tattoo system that has many of the advantages of the tattoo machines mentioned heretofore and many novel features that result in a new tattoo system which is not anticipated, rendered obvious, suggested, or even implied by any of the prior art tattoo machines, either alone or in any combination thereof.

To attain this, the present invention generally comprises a tube member having a tapered neck with exterior threading at a distal end thereof, and a tip member threadably attached to the tube member. The tip member is comprised of a center body, a rear portion having a tapering rear lip and a rear opening, a front portion with a front opening, a reservoir connected between the front opening and the rear opening, and interior threading within a central portion of said reservoir for threadably engaging the exterior threading. The tip member is preferably comprised of a plastic to sealably engage the tube member. The front portion of the tip member is preferably tapered with the front opening slightly larger than the needle reciprocating through thereof.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a tattoo system that will overcome the shortcomings of the prior art devices.

A second object is to provide a tattoo system for providing a disposable tip that allows for efficient cleaning and tattooing.

Another object is to provide a tattoo system that reduces the amount of time to apply a tattoo to the skin.

An additional object is to provide a tattoo system that increases the sanitation of the tattoo applicator.

A further object is to provide a tattoo system that reduces the likelihood of ink and blood being drawn into the tube portion of the tattoo machine. Another object is to provide a tattoo system that allows for easy color changing of the tattoo machine.

A further object is to provide a tattoo system that reduces the amount of excess ink upon the upper surface of the skin thereby increasing the tattoo artist's ability to apply a tattoo.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DESCRIPTION OF THE PREFERRED EMBODIMENT

Turning now descriptively to the drawings, in which similar reference characters denote similar elements throughout the several views, FIGS. 1 through 9 illustrate a tattoo system 10, which comprises a tube member 20 having a tapered neck 28 with exterior threading 26 at a distal end thereof, and a tip member 30 threadably attached to the tube member 20. The tip member 30 is comprised of a center body 32, a rear portion 34 having a tapering rear lip 38 and a rear opening 46, a front portion 36 with a front opening 40, a reservoir 42 connected between the front opening 40 and the rear opening 46, and interior threading 44 within a central portion of said reservoir 42 for threadably engaging the exterior threading 26. The tip member 30 is preferably comprised of a plastic to sealably engage the tube member 20. The front portion 36 of the tip member 30 is preferably tapered with the front opening 40 slightly larger than the needle 24 reciprocating through thereof.

As shown in FIGS. 2, 3, 5 and 6 of the drawings, the tube member 20 is comprised of an elongate rigid structure having a first end and a second end. The tube member 20 is preferably constructed of a metal such as stainless steel, however various other types of materials may be utilized.

Figure 1:
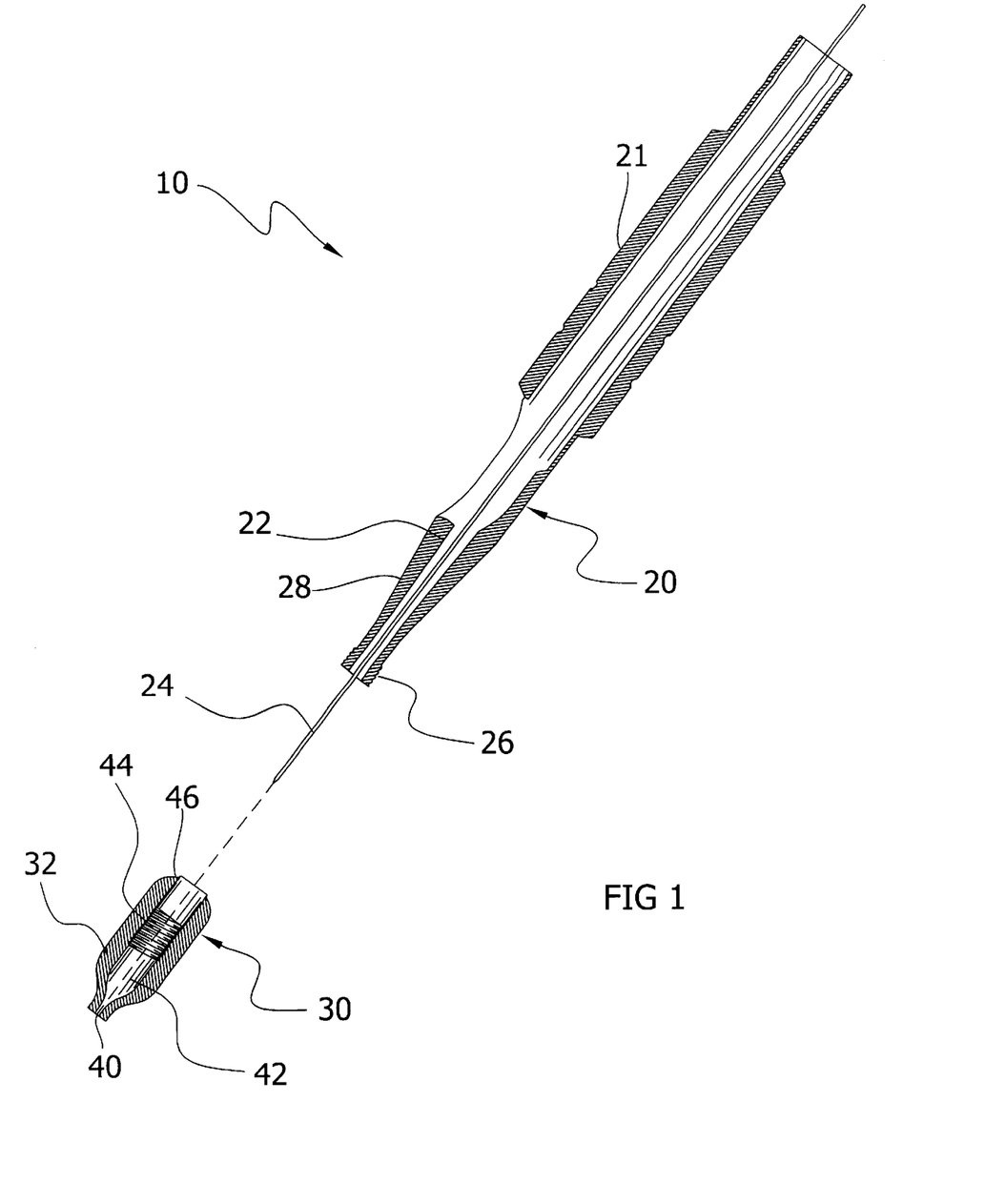
FIG. 1 is an exploded side cutaway view of the present invention.
Figure 2:
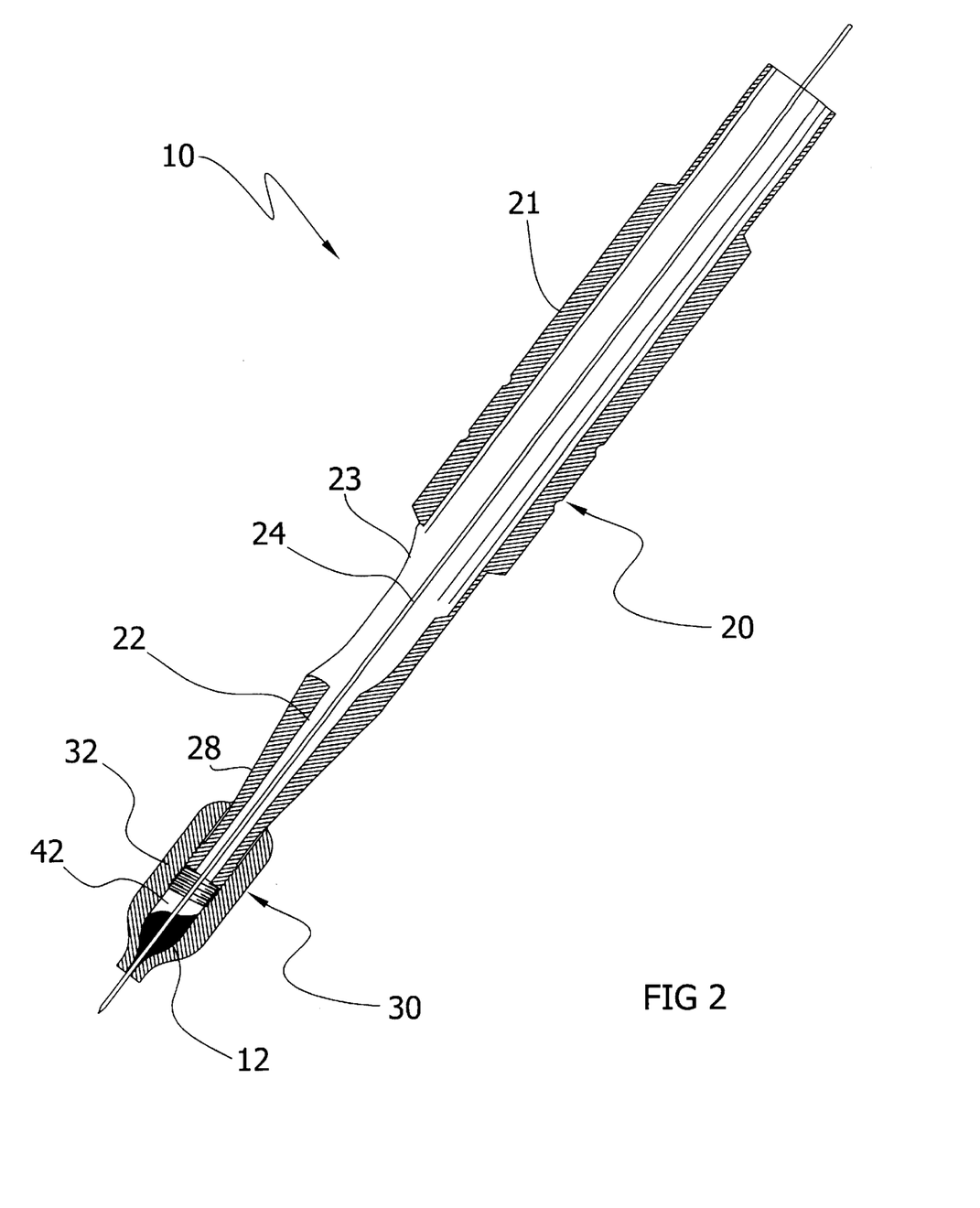
FIG. 2 is a side cutaway view of the present invention.
Figure 6:
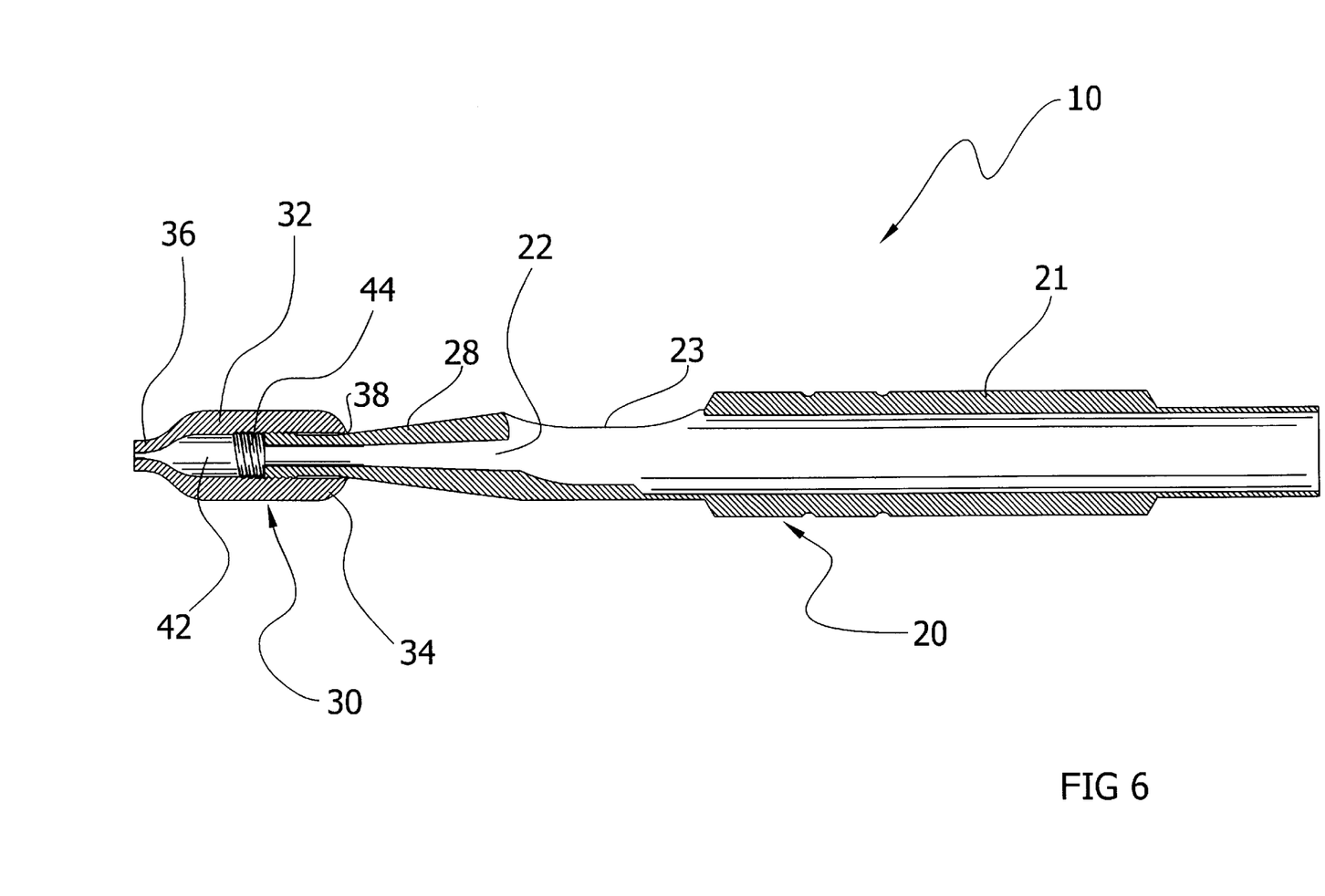
FIG. 6 is a cross sectional view taken along line 6—6 of FIG. 5.

The tube member 20 has a body portion 21 and a tapered neck 28 extending from the body portion 21 as best shown in FIG. 6 of the drawings. The tapered neck 28 preferably has a gradual slope which may be straight or curved in portions thereof. A center channel 22 extending longitudinally within the tube member 20 for receiving the needle 24. The needle 24 extends through the channel 22 from the first end of the tube member 20 through the second end thereof. The second end of the tube member 20 has exterior threading 26 for threadably receiving the tip member 30 as shown in FIGS. 1 and 2 of the drawings. The needle 24 may be comprised of a solid structure as is well known in the art.

An electric powered drive unit is attached to the first end of the tube member 20 and attached to the end of the needle 24 in order to reciprocate the needle 24. Drive units for tattoo machines are well known in the art and further discussion of tattoo machines is not required to explain the present invention. An access opening 23 near the tapered neck 28 of the tube member 20 provides access for cleaning the channel 22 after usage. The tube member 20 may also have various shapes and structures other than that illustrated in the drawings.

Figure 3:
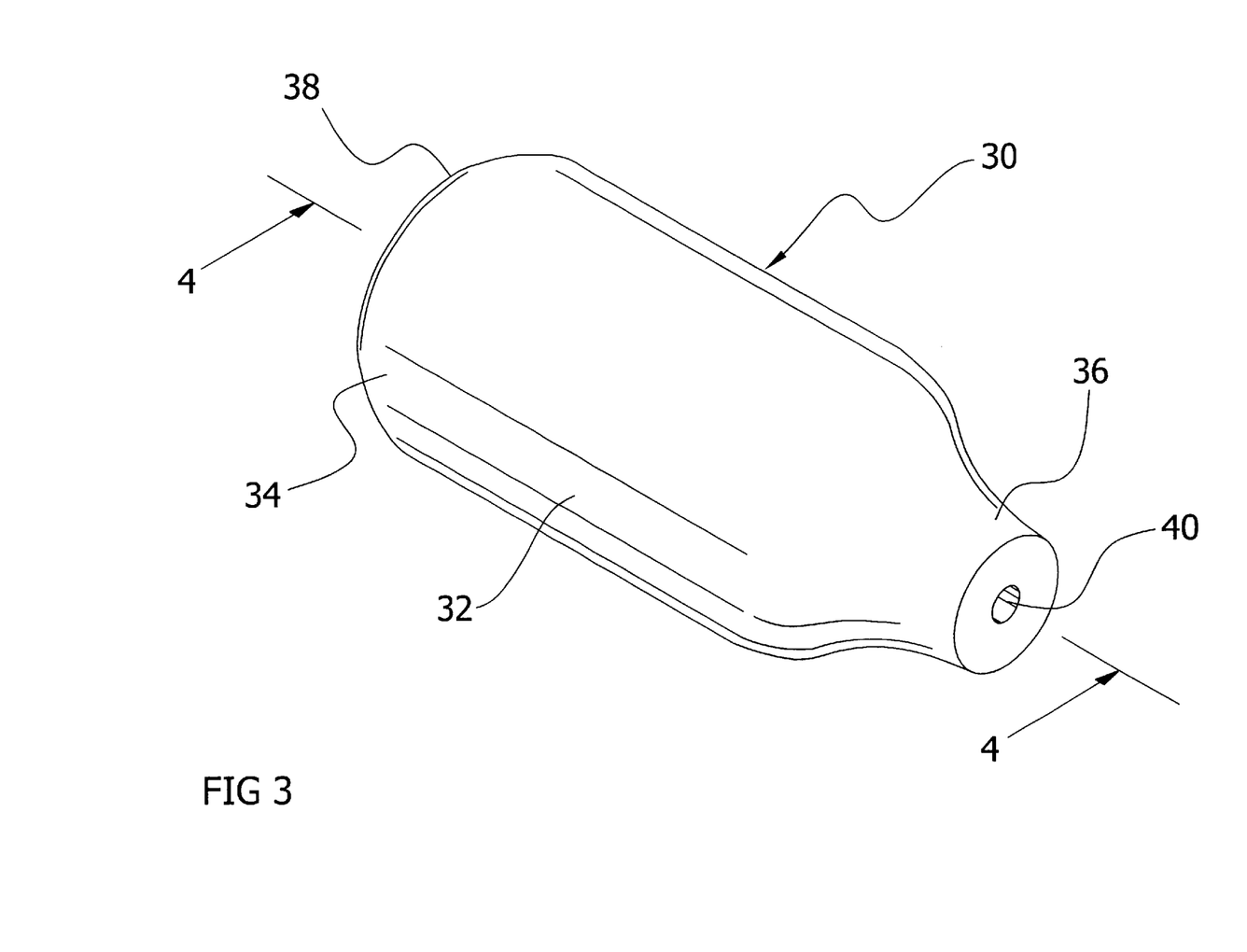
FIG. 3 is an upper perspective view of the disposable tip member.
Figure 7:
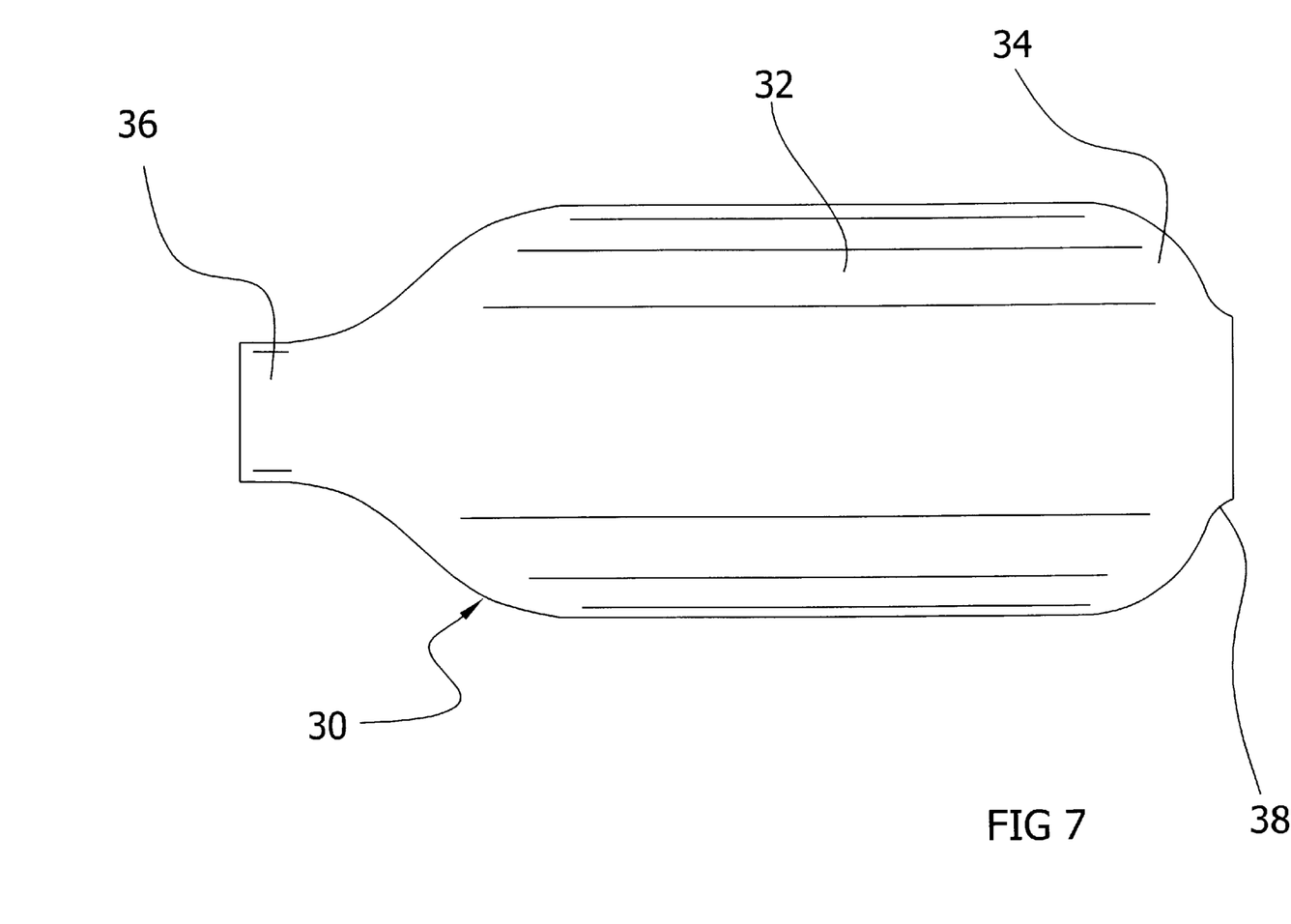
FIG. 7 is a side view of the disposable tip member.
Figure 8:
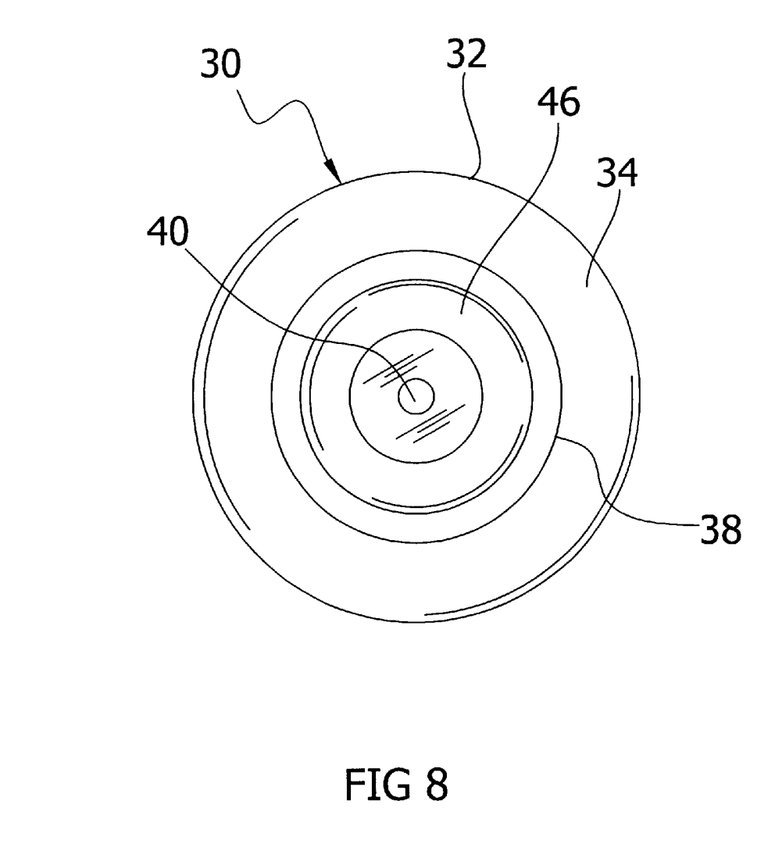
FIG. 8 is a rear view of the disposable tip member.
Figure 9:
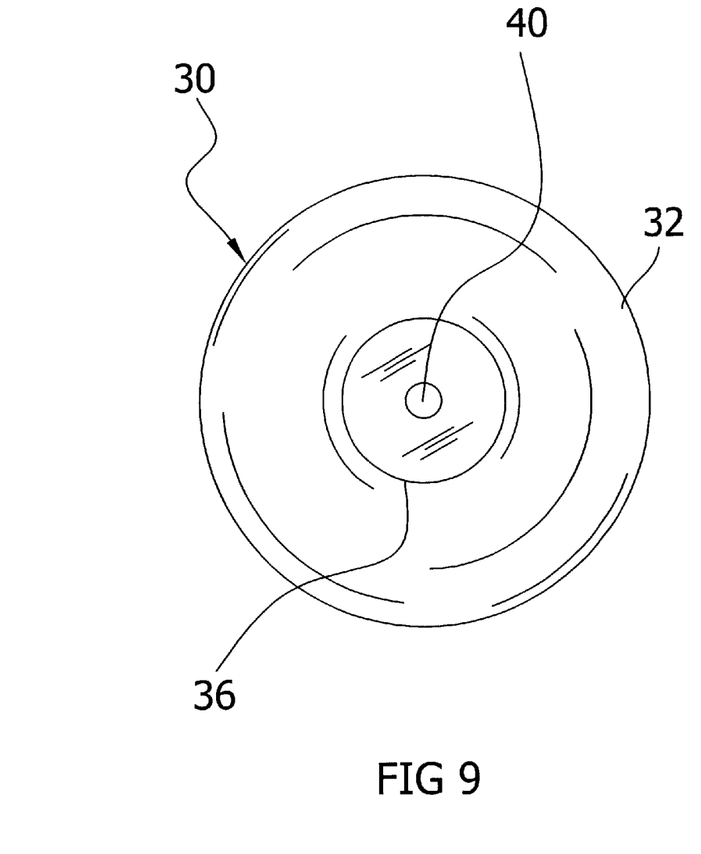
FIG. 9 is a front view of the disposable tip member.

As shown in FIGS. 3 and 7 of the drawings, the tip member 30 is comprised of a center body 32, a rear portion 34 having a tapering rear lip 38 and a rear opening 46, a front portion 36 with a front opening 40, a reservoir 42 connected between the front opening 40 and the rear opening 46, and interior threading 44 within a central portion of said reservoir 42 for threadably engaging the exterior threading 26. The tip member 30 is preferably constructed of a translucent plastic or similar material for reducing the cost of production. The tip member 30 is preferably constructed so as to be disposable after a one-time usage thereof.

Figure 4:
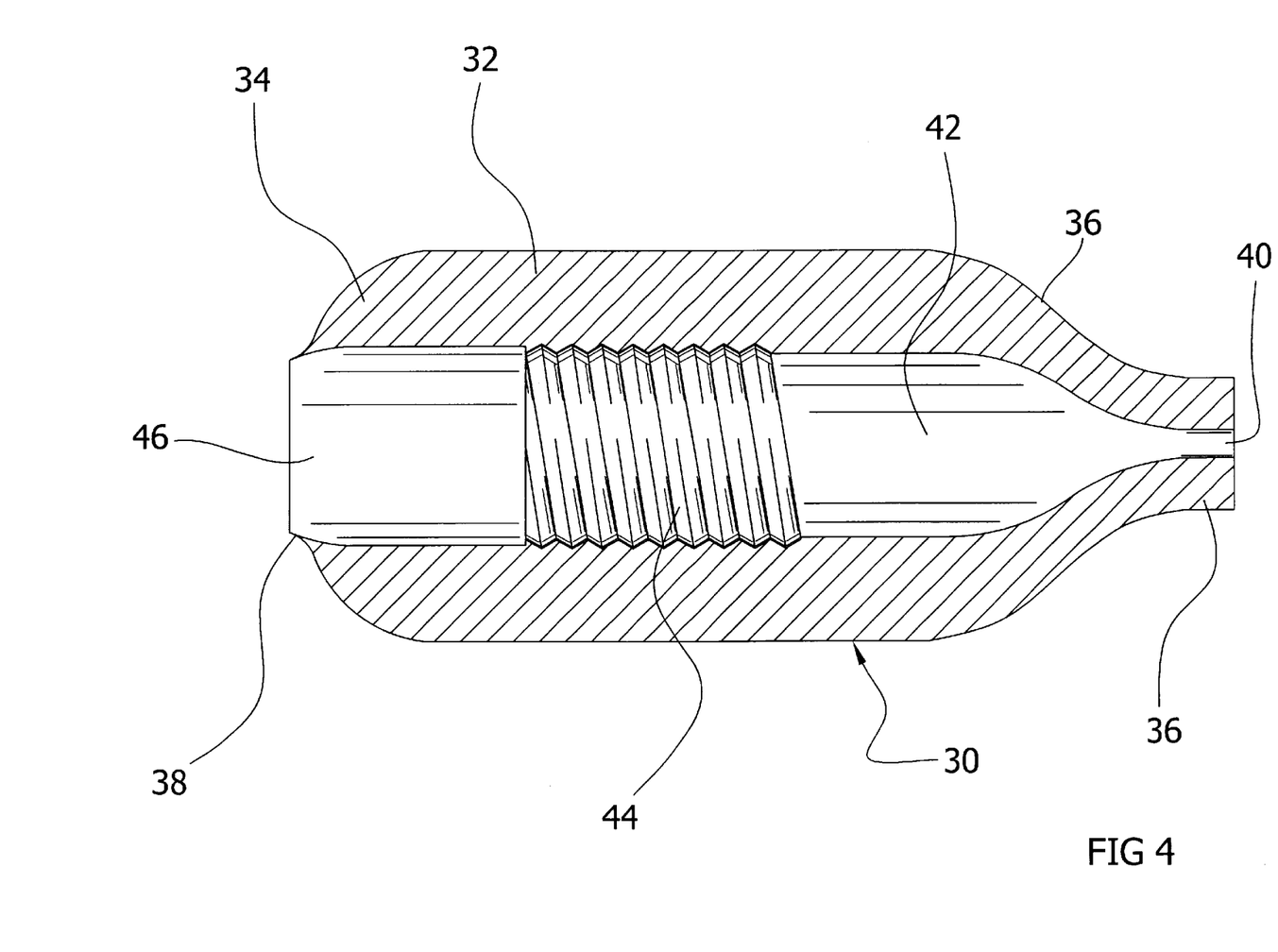
FIG. 4 is a cross sectional view taken along line 4—4 of FIG. 3.
Figure 5:
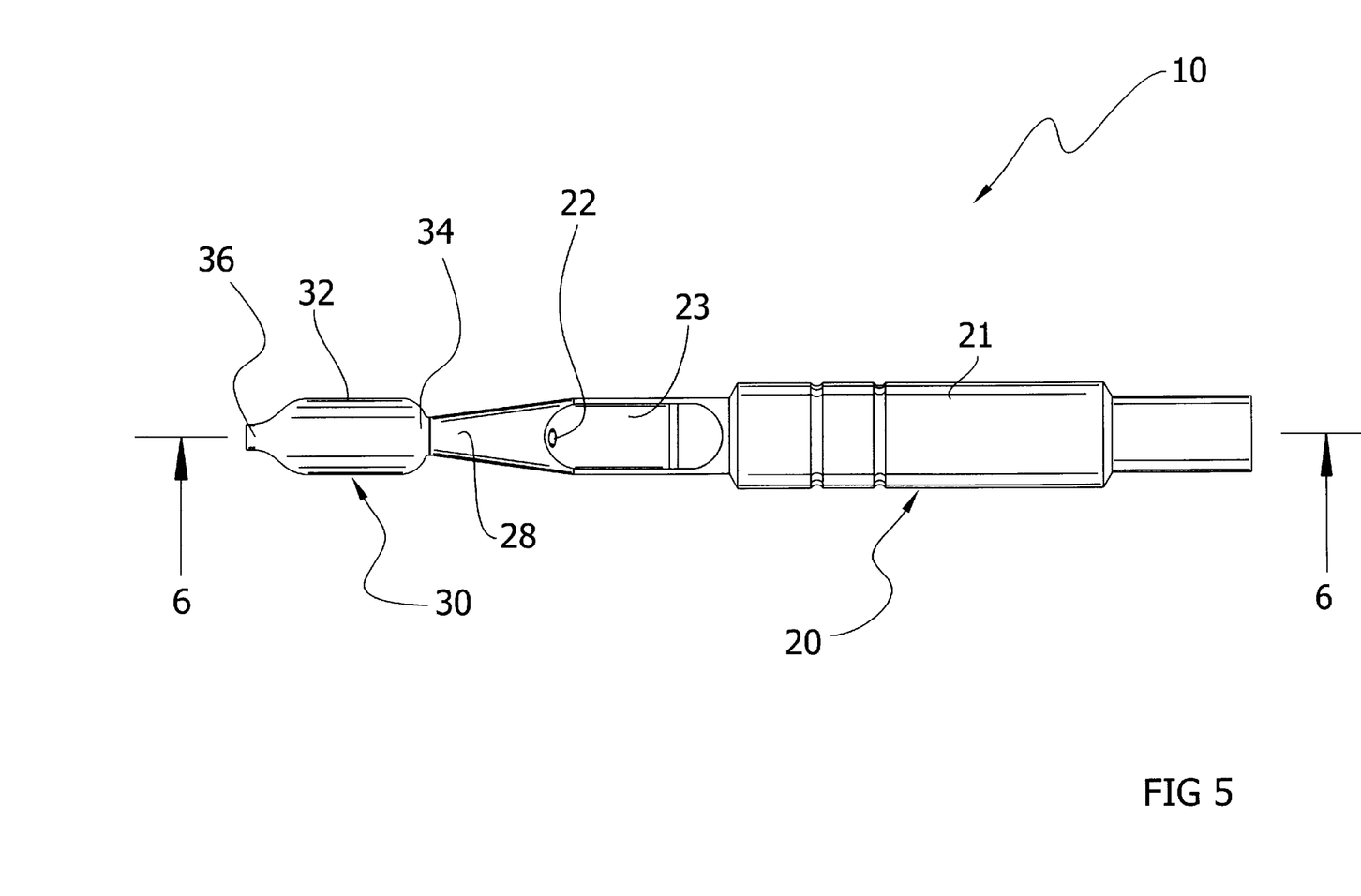
FIG. 5 is a top view of the present invention.

As best shown in FIGS. 4 and 7 of the drawings, the front portion 36 of the tip member 30 is preferably tapered from the center body 32. As best illustrated in FIG. 4 of the drawings, the front portion 36 has a front end that extends a finite distance wherein the front end has a constant diameter as shown in FIG. 4 of the drawings. The front opening 40 is slightly larger than the needle 24 reciprocating through thereof for allowing ink 12 to remain upon the distal end of the needle 24 when exiting the tip member 30. The front opening 40 preferably has a constant diameter within the front end of the tip member 30 as best shown in FIG. 4 of the drawings.

The reservoir 42 within the tip member 30 extends concentrically from the front opening 40 rearwardly to the rear opening 46 within the tip member 30. The reservoir 42 preferably broadens from the front opening 40 to a constant diameter as shown in FIG. 4 of the drawings. The reservoir 42 has a sufficient volume to receive an acceptable amount of ink 12 to be utilized within the tattoo procedure.

As shown in FIG. 4 of the drawings, an interior threading 44 extends within the central portion of the reservoir 42 for threadably engaging the exterior threading 26 of the tube member 20. The interior threading 44 is positioned a finite distance from the front opening 40 and a finite distance from the rear opening 46 as further shown in FIG. 4 of the drawings.

As shown in FIGS. 4 and 7 of the drawings, a rear lip 38 extends from the rear portion 34, wherein the rear portion 34 is tapered. The rear lip 38 extends rearwardly and inwardly from the rear portion 34 as best shown in FIG. 4 of the drawings. The rear lip 38 reduces the diameter of the reservoir 42 thereby providing a secondary seal adjacent the tapered neck 28 as shown-in FIGS. 4 and 6. The rear lip 38 prevents ink 12 that accidentally passes through the threading 26, 44 from escaping about the outside of the tip member 30 thereby preventing contamination of the skin and the tube member 20.

In use, the user threadably secures the tip member 30 to the exterior threading 26 of the tube member 20 as shown in FIG. 2 of the drawings. The connection of the threading 26, 44 in effect creates a main reservoir 42 and a secondary compartment. The needle 24 extends through the front opening 40 of the tip member 30 as best shown in FIG. 2 of the drawings. The pointed end of the needle 24 extends a finite distance from the front end of the tip member 30 when fully extended as shown in FIG. 2 of the drawings. The user then draws ink 12 into the reservoir 42 as shown in FIG. 2 of the drawings. The user then operates the tattoo system 10 with the electric motor reciprocating the needle 24 while the user "draws" the tattoo design within the skin of the client. When finished, the user removes the tip member 30 and disposes of the contaminated tip member 30 accordingly. The user then cleans the tube member 20 and then secures a new tip member 30 to the tube member 20 for a different color or client.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed to be within the expertise of those skilled in the art, and all equivalent structural variations and relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A tattoo system, comprising:
   a tube member having a first end for receiving a drive unit, a threaded end and a center channel for receiving an elongate needle; and
   a tip member having a front opening, a rear opening and a reservoir between said openings, wherein said tip member is threadably attachable to said threaded end of said tube member, wherein said tip member is comprised of a center body, a rear portion extending from said center body having said rear opening, and a front portion extending from said center body having said front opening, wherein said rear portion includes a tapering rear lip that extends rearwardly and inwardly from said rear portion for creating a seal against a tapered neck of said tube member.

2. The tattoo system of claim 1, wherein said reservoir includes an interior threading for threadably engaging said threaded end of said tube member.

3. The tattoo system of claim 2, wherein said interior threading is centrally positioned within said reservoir thereby creating a main reservoir fluidly connected to said front opening and a secondary reservoir on opposing sides of said threaded end of said tube member.

4. The tattoo system of claim 1, wherein said front portion is tapered.

5. The tattoo system of claim 1, wherein said front portion has a front end that has a constant outer diameter and a constant inner diameter for said front opening.

6. The tattoo system of claim 1, wherein said front opening is slightly larger than said needle.

7. The tattoo system of claim 1, wherein said tip member is comprised of a plastic material.

8. The tattoo system of claim 1, wherein said reservoir is comprised of a constant diameter within a central portion and a tapered structure towards said front opening.

9. A tattoo system, comprising:
   a tube member having a first end for receiving a drive unit, a tapered neck having a threaded end, a center channel for receiving an elongate needle, and an access opening extending into the tube member into said center channel; and
   tip member having a front opening, a rear opening and a reservoir between said openings, wherein said tip member is threadably attachable to said threaded end of said tube member.

10. The tattoo system of claim 9, wherein said reservoir includes an interior threading for threadably engaging said threaded end of said tube member.

11. The tattoo system of claim 10, wherein said interior threading is centrally positioned within said reservoir thereby creating a main reservoir fluidly connected to said front opening and a secondary reservoir on opposing sides of said threaded end of said tube member.

12. The tattoo system of claim 9, wherein said front portion is tapered.

13. The tattoo system of claim 9, wherein said front portion has a front end that has a constant outer diameter and a constant inner diameter for said front opening.

14. The tattoo system of claim 9, wherein said front opening is slightly larger than said needle.

15. The tattoo system of claim 9, wherein said tip member is comprised of a plastic material.

16. The tattoo system of claim 9, wherein said reservoir is comprised of a constant diameter within a central portion and a tapered structure towards said front opening.

* * * * *